United States Patent [19]

Ferkany et al.

[11] Patent Number: 4,928,453
[45] Date of Patent: May 29, 1990

[54] APPARATUS FOR TRANSFERRING ELONGATED SAMPLE TUBE HOLDERS TO AND FROM WORKSTATIONS

[75] Inventor: Michael A. Ferkany, Southfield, Mich.; William J. Kinnier, Timonium, Md.

[73] Assignee: Biomedical Devices Company, Inc., Farmington, Mich.

[21] Appl. No.: 138,875

[22] Filed: Dec. 29, 1987

[51] Int. Cl.$^5$ .................. B65B 57/04; B65B 61/00; B65B 3/04
[52] U.S. Cl. ................................ 53/67; 53/137; 53/281; 53/317; 198/341; 198/464.2
[58] Field of Search .............................. 53/67, 71, 281; 198/464.2, 857, 341

[56] References Cited

U.S. PATENT DOCUMENTS

| | | |
|---|---|---|
| 1,866,369 | 7/1932 | Podel . |
| 1,956,218 | 7/1932 | Huntley et al. . |
| 1,957,464 | 5/1934 | Lloyd et al. . |
| 2,139,573 | 12/1938 | Booth . |
| 2,652,137 | 9/1953 | Taranto . |
| 3,100,957 | 8/1963 | King et al. . |
| 3,214,887 | 11/1965 | Weller . |
| 3,239,216 | 3/1966 | Pfleger .................... 198/464.2 X |
| 3,382,646 | 5/1968 | Leudtke et al. . |
| 3,552,536 | 1/1971 | Emary . |
| 3,578,142 | 5/1971 | Burgess, Jr. . |
| 3,651,985 | 3/1972 | Smith ....................... 198/464.2 X |
| 3,656,605 | 4/1972 | Gess . |
| 3,811,548 | 5/1974 | Neff . |
| 4,029,961 | 6/1977 | Lohr et al. . |
| 4,040,533 | 8/1977 | De Boer et al. . |
| 4,147,250 | 4/1979 | Schultz . |
| 4,488,633 | 12/1984 | Kampf . |
| 4,503,964 | 3/1985 | Kampf et al. . |

Primary Examiner—John Sipos
Attorney, Agent, or Firm—Finnegan, Henderson, Farabow, Garrett & Dunner

[57] ABSTRACT

A method and apparatus for transferring sample holders to and from workstations positioned along a transfer path, including an entrance support having a first transfer for supplying the sample holders to the transfer path, an exit support for receiving the sample holders from the transfer path, a second transfer for transferring the sample holders along the transfer path past the workstations and a controller for coordinating the actuation of the first and second transfers and the workstations.

38 Claims, 10 Drawing Sheets

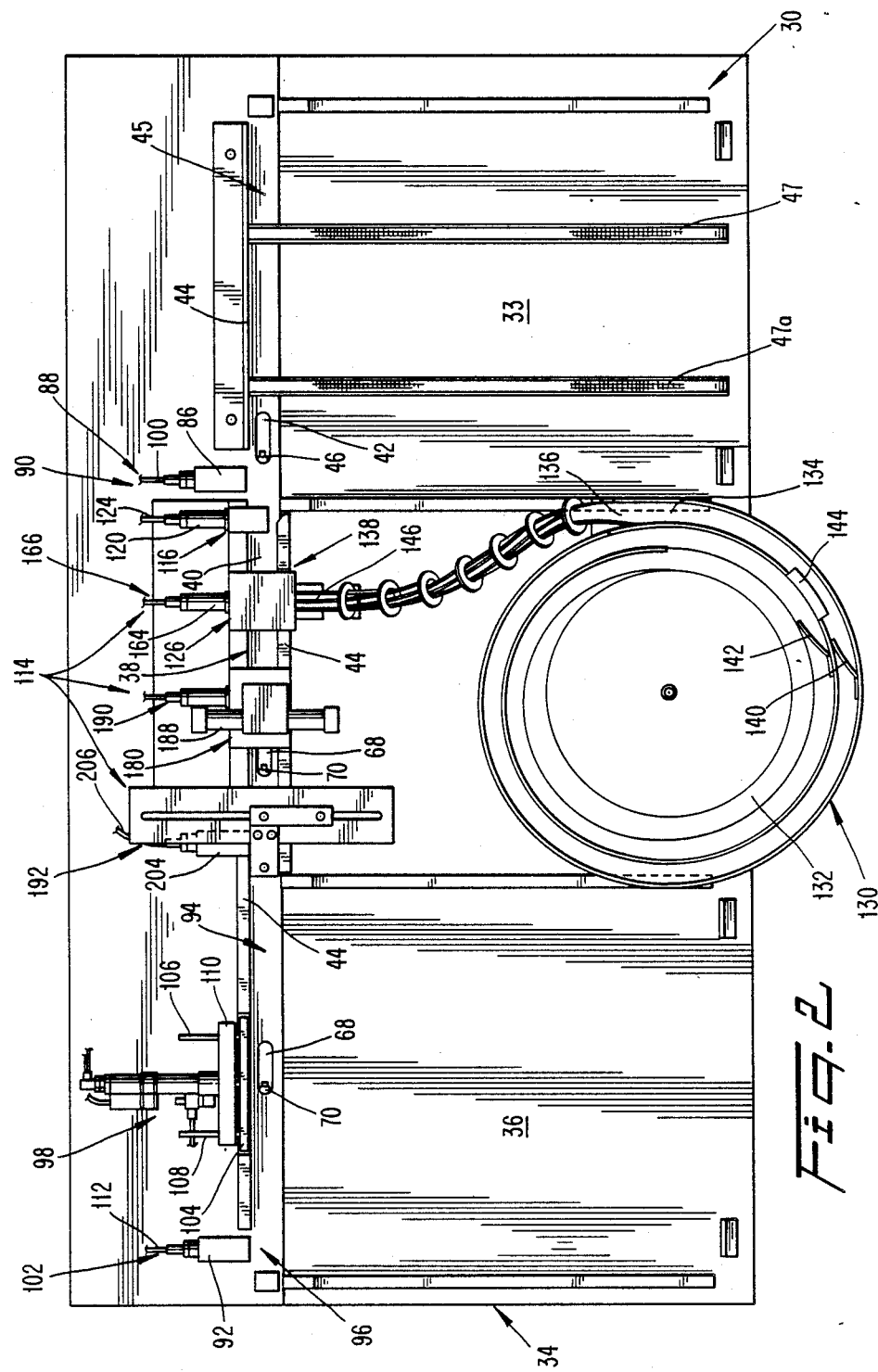

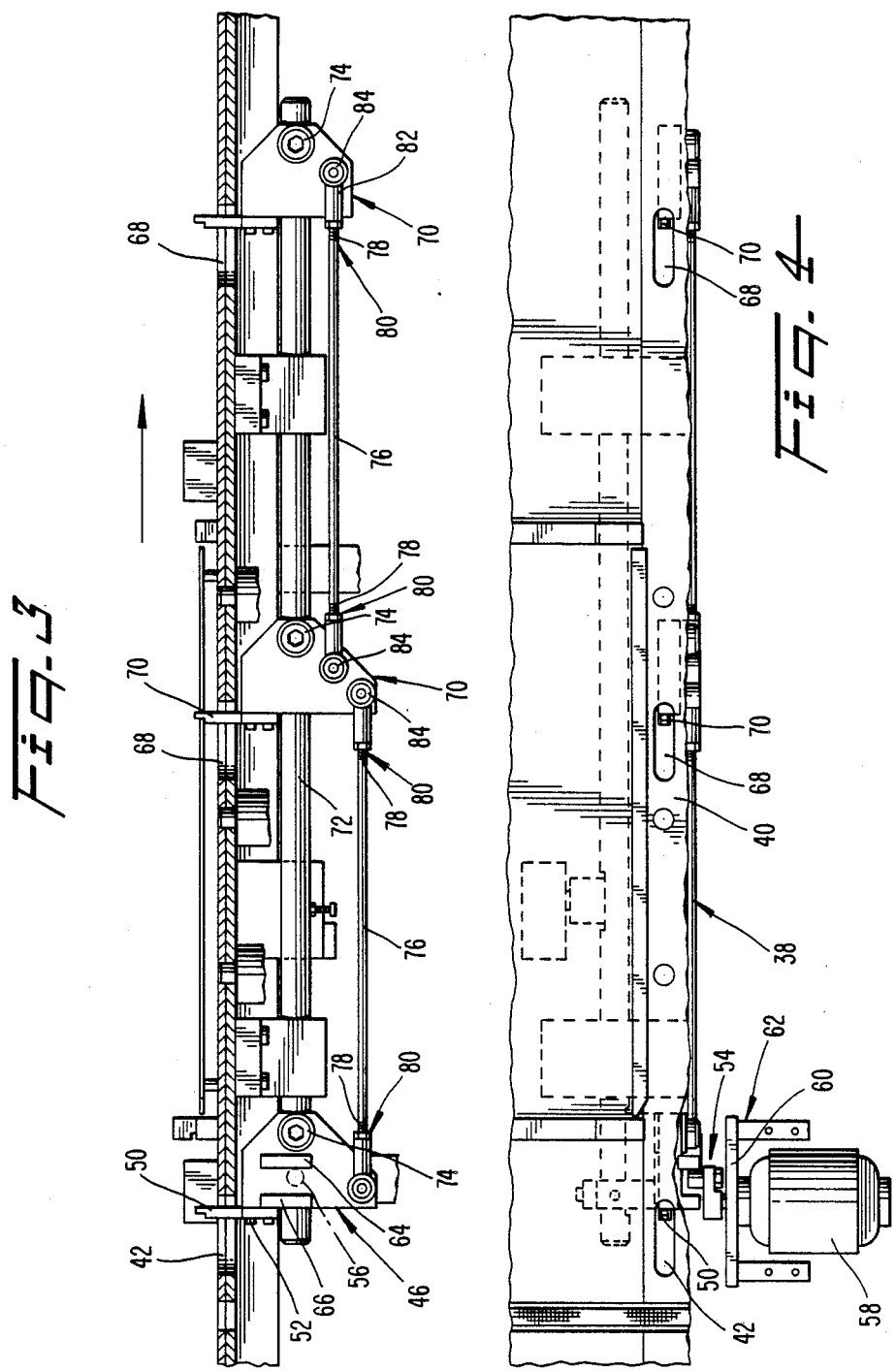

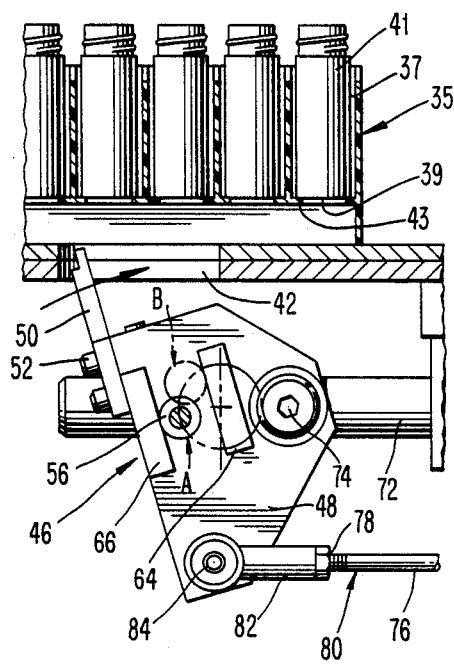
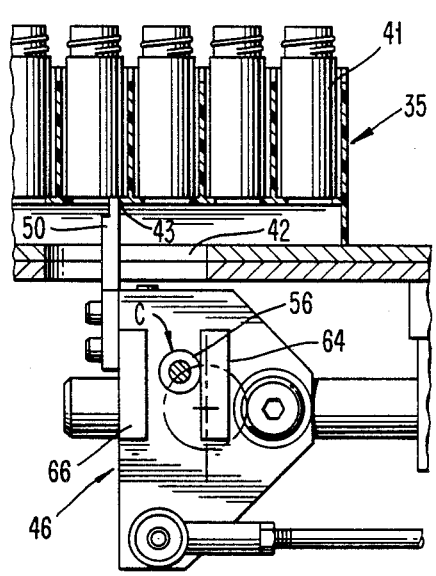
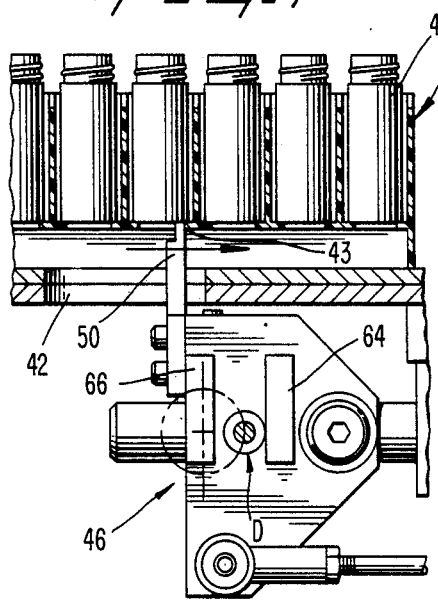
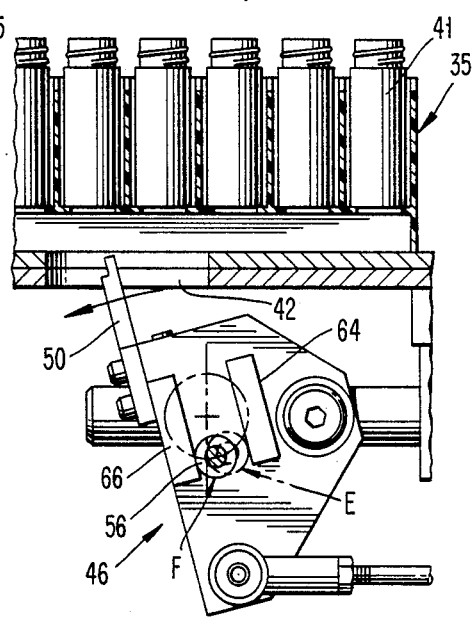

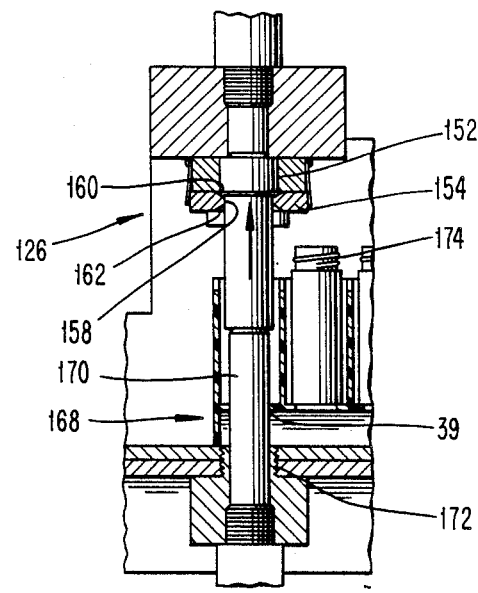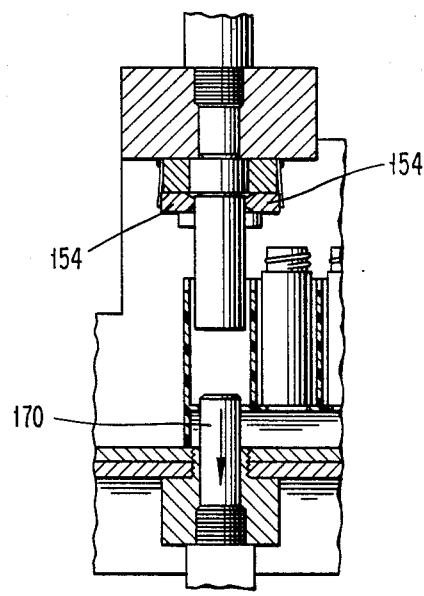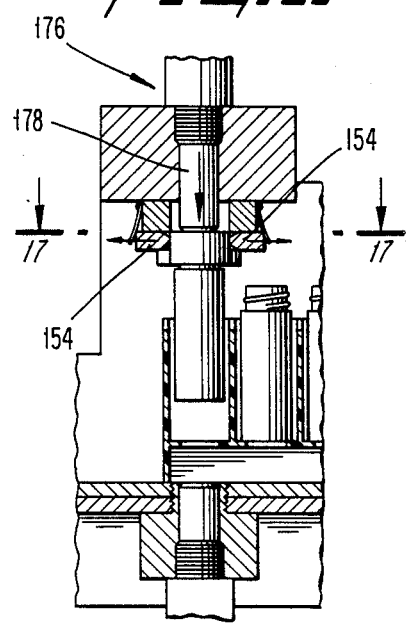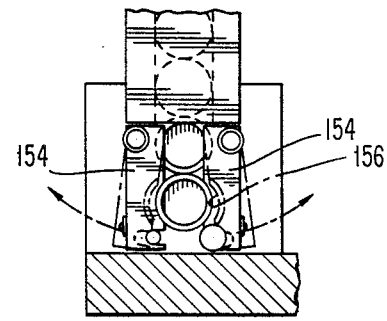

APPARATUS FOR TRANSFERRING ELONGATED SAMPLE TUBE HOLDERS TO AND FROM WORKSTATIONS

BACKGROUND OF THE INVENTION

The invention relates to devices for transferring articles and, in particular, the invention pertains to an apparatus for moving sample holders past a series of operating stations.

Conventional transfer devices generally include endless belt or chain arrangements having pins or extensions for engaging the articles along an opening and transferring the articles about a predetermined path. The endless belt or chain is driven by a stepper motor which stops the article intermittently so that particular functions may be performed at the workstations.

A problem encountered in the conventional transfer devices is the misalignment between the engaging elements of the endless belt or chain and the articles being transferred. For example, the articles may include a sample holder having a row of compartments for containing the sample tubes, so that the engaging portion of the belt engages the holder along an opening for moving the sample holder along the path of the chain. However, if the engaging element fails to engage the opening, the holder becomes misaligned, thereby requiring the transfer operation to be stopped until the holder is reset.

Misalignment occurs even more frequently when the sample holder is transferred by frictional engagement between a belt and the holder, i.e., without engaging elements disposed along the chain or belt to engage openings in the sample holders. Not surprisingly, the friction between the sample holder and the chain or belt in this situation is generally insufficient to transfer the sample holders with the requisite precision. Therefore, such transfer devices typically require resetting to ensure the samples are aligned with the appropriate workstation.

Thus, another problem with these stepper motor controlled devices is that they require precision position sensing devices, position feedback circuits, and an alignment correction function, which is usually microprocessor controlled, in order to correct for cumulative position errors.

Another problem with conventional transfer devices concerns the manner in which the sample holders are deposited into the transfer path which goes past the workstations. For example, in some conventional devices, a first belt drives the sample holders in a first direction toward a wall having a workstation placed therealong, while a second endless belt or chain with projections engages the sample holder for transfer against the wall in a second direction at a 90° angle from the first direction, to move the sample holder past the workstation. Although the second end less belt may be driven by a stepper motor, thereby providing intermittent movement, the first belt is driven continuously so that sample holders are pushed up against each other in the areas where they are deposited by the first transfer belt to the second transfer belt. Such an arrangement fails to provide any timing for introducing sample holders to the workstation transfer and results in the unnecessary continuous driving of the sample holders against an end wall.

Another problem with the prior art is the failure to provide a timing and monitoring apparatus for coordinating operations at a plurality of workstations.

SUMMARY OF THE INVENTION

Accordingly, it is an object of this invention to eliminate the difficulties encountered in conventional transfer devices and thereby provide a system for accurately and effectively conveying sample holders along a transfer path.

It is another object of the present invention to provide a transfer device for engaging consecutive sample holders along the transfer path in a timed sequence and for transferring and delivering each of the sample holders to a workstation.

It is another object of the present invention to provide a method for conveying a plurality of sample holders individually along a transfer path, so that each of the sample holders travel consecutively to individual workstations.

Additional objects and advantages of the invention will be set forth in part in the description which follows, and in part will be obvious from the description, or may be learned by practice of the invention. The objects and advantages of the invention may be realized and attained by means of the instrumentalities and combinations particularly pointed out in the appended claims.

To achieve the objects and purposes of the invention, as embodied and broadly described herein, the invention relates to a device for transferring an article to and from at least one operating station positioned along a transfer path and having an entrance support for supplying the article to the transfer path and an exit support for receiving the article from the transfer path, comprising: support means extending between the entrance support and the exit support for supporting the article during transfer to and from each operating station, the support means including a primary elongated aperture; guide means disposed along the support means for guiding the article along the transfer path; and transfer means disposed along the support means for engagement with the article to transfer the article a predetermined amount along the transfer path, the transfer means including a primary transfer member pivotally mounted to pivot within the primary elongated aperture and to engage the article, thereby transferring the article along the transfer path.

To further achieve the objects and purposes of the invention, as embodied and broadly described herein, the invention also relates to a device for transferring sample tubes arranged in elongated sample holders to and from consecutive workstations positioned along a transfer path, comprising: entrance support means for supplying said sample holders prior to said transfer path; exit support means for receiving the sample holders from the transfer path; workstation support means extending between the entrance support means and the exit support means for supporting the sample holder during transfer to and from the workstations, the workstation support means defining an entrance area for receiving the sample holders from the entrance support means; guide means disposed along the workstation support means for guiding the sample holders within the workstation support means toward the exit support means; first transfer means disposed along the entrance support means for transferring each of the sample holders individually into the entrance area of the workstation support means; second transfer means disposed along the workstation support means for engaging the sample holders to transfer the sample holders a predetermined amount along the workstation support means; and control means for coordinating actuation of the first transfer means, the second transfer means and the workstations to ensure smooth operation of the device.

The invention resides in the novel parts, constructions, arrangements, combinations and improvements shown and described. The accompanying drawings, which are incorporated in and constitute a part of this specification, illustrate the presently preferred embodiment of the invention and, together with the description, serve to explain the principles of the invention.

BRIEF DESCRIPTION OF THE DRAWINGS

FIG. 2 is a top view of FIG. 1.

FIG. 3 is a rear view of a portion of the device shown in FIG. 1.

FIG. 4 is a top view of FIG. 3.

FIG. 5 is an enlarged view of a primary transfer member of the preferred embodiment of the invention shown in FIG. 1.

FIG. 6 is a view similar to FIG. 5 and shows the primary transfer member in an upright position in engagement with a sample holder.

FIG. 7 is a view similar to FIG. 5 and shows the primary transfer member transferring a sample holder.

FIG. 8 is a view similar to FIG. 5 and shows the primary transfer member retracting from the sample holder.

FIG. 14 is an enlarged view of the capping workstation shown in FIG. 12 and shows a sample tube being pushed into a cap by an elevator at the capping workstation.

FIG. 15 is a view similar to FIG. 14 and shows the sample tube and cap suspended at the capping workstation.

FIG. 16 is a view similar to FIG. 14 and shows the sample tube and cap being deposited back into a compartment of the sample holder.

FIG. 17 is a view of a portion of the capping workstation taken along line 17—17 of FIG. 16.

DESCRIPTION OF THE PREFERRED EMBODIMENT

Figure 1:
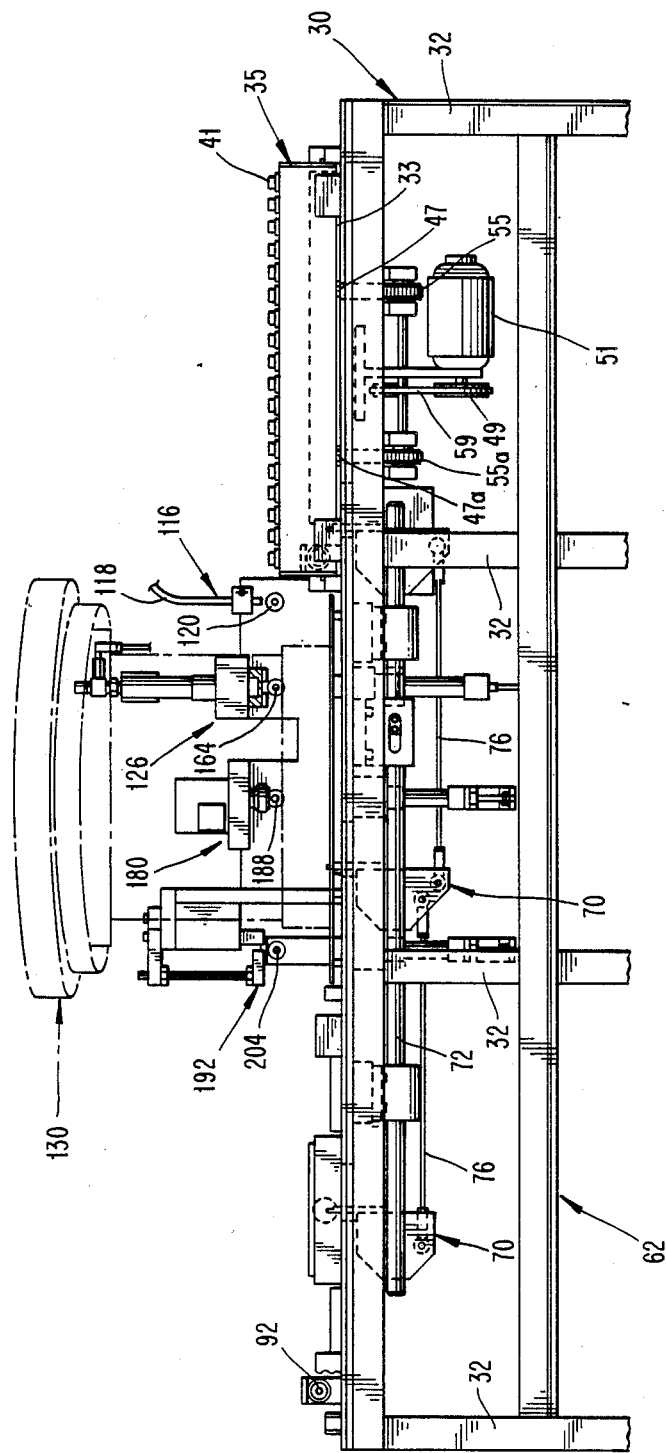
FIG. 1 is a front view of a preferred embodiment of the transfer device of the invention.

Reference will now be made in detail to the present preferred embodiment of the invention, an example of which is illustrated in the accompanying drawings. Wherever possible, the same reference numerals will be used throughout the drawings to refer to the same or like parts.

Referring to FIGS. 1–4, it may be seen that the transfer mechanism is useful for transferring articles along a transfer path between an entrance support means and an exit support means, the transfer path having one or more workstations positioned therealong.

In accordance with the invention, the device includes an entrance support means for supporting the articles during the transfer of the articles to the transfer path. As here embodied, the entrance support means is an entrance support table 30 for accommodating a plurality of articles and having support legs 32 and support surface 33.

In accordance with the invention, an exit support means is provided for receiving the articles after transfer to and from the workstations along the transfer path. As here embodied, and referring particularly to FIG. 2, the exit support means includes an exit support table 34 supported by support legs 32 and having a support surface 36. Preferably, the width of the entrance support table 30 and the exit support table 34 corresponds substantially to the width of the articles, and the length of the tables 30 and 34 corresponds to an amount necessary to accommodate a desired number of articles.

In accordance with the invention, a workstation support means is provided between the entrance support means and the exit support means for supporting the articles during transfer to and from one or more workstations. As here embodied, and referring particularly to FIG. 2, the workstation support means includes a workstation support surface 38 including a channel-like track 40 also supported by support legs 32. As here embodied, a primary elongated aperture 42 is provided along the workstation support surface 38.

In accordance with the invention, guide means are disposed along the workstation support for guiding the articles during transfer from the entrance support to the exit support. As embodied herein, the guide means include guide rails 44 disposed along the workstation support surface 38.

As here embodied, and referring particularly to FIGS. 5–8, the articles are sample holders 35 having a row of compartments 37, each compartment having an opening 39 at the bottom thereof and each compartment 37 adapted for receiving a sample tube 41. Preferably, the opening 39 has a smaller diameter than the sample tube 41 so that the tube is supported by the edge 43 of the opening 39.

Figure 9:
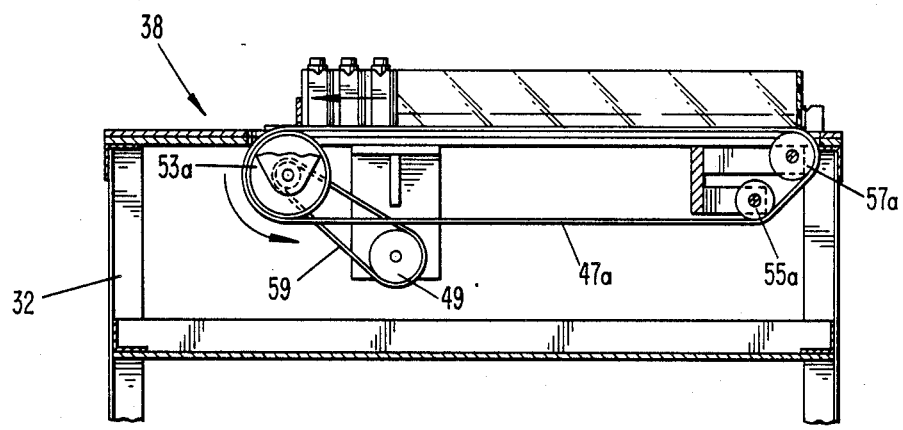
FIG. 9 is a side view of an entrance support shown in FIGS. 1 and 2.

In accordance with the invention, a first transfer means is provided for transferring each of the sample holders from the entrance support means to the workstation support. As here embodied, and as shown in FIGS. 1, 2 and 9, the first transfer means is disposed along the entrance support table 30 for transferring sample holders 35 individually into an entrance area 45 of the workstation support surface 38. Preferably, the first transfer means includes two endless belts 47 and 47a disposed for movement along the surface 33 of the entrance support table 30.

The endless belts 47 and 47a are arranged on a plurality of rollers 53, 55, 57 and 53a, 55a and 57a, respectively (FIG. 9). An additional roller 49 is driven by a motor 51 (FIG. 1) for driving the endless belts 47 and 47a around the rollers 53, 55, 57 and 53a, 55a, 57a, respectively. As shown in FIG. 9, a driving belt 59 may be provided for drivingly connecting the drive roller 49 and the rollers 53, 55, 57 and 53a, 55a, 57a. As the endless belts 47, 47a are driven by the motor 51 along the support surface 33 of the entrance support table 30, they urge the sample holders 35, also arranged on the support surface 33 of the entrance support table 30, toward the entrance area 45 of the workstation support surface 38.

In accordance with the invention, a second transfer is disposed along the workstation support surface for engaging the sample holders to transfer the sample holders a predetermined amount along the transfer path. As here embodied, and referring to FIGS. 1-4, the second transfer means includes a primary transfer member 46 pivotally mounted to pivot within the primary elongated aperture 42 in the workstation support surface 38 for engaging the sample holders 35. The primary transfer member 46 includes a primary transfer block 48 and a finger-like extension 50 fixed by conventional means, such as a bolt 52, to the primary transfer block 48. The finger-like extension 50 of the primary transfer member 46 moves within the primary elongated aperture 42 and into an opening 39 in the sample holder 35 for engaging an edge 43 of the opening 39 and transferring the sample holder 35 along the transfer path.

As here embodied, the second transfer means also includes cam means for pivoting the primary transfer member 46. Referring to FIGS. 4-8, the cam means includes a cam 56 rotatably driven by conventional means, such as a motor 58. The cam 56 and motor 58 are supported by a support bracket 60 on a support frame characterized generally as 62.

As here embodied, the cam means also includes camming surfaces disposed on the primary transfer block 48. Preferably, the camming surfaces include a forward block 64 and a rear block 66 arranged in vertical and spaced relation with respect to each other on the primary transfer member block 48. The blocks 64 and 66 may be fixed to the primary transfer member block 48 by conventional means, such as bolts or the like. The cam 56 rotates between these two spaced blocks and engages the blocks 64, 66 to pivot the primary transfer member 46.

Specifically referring to FIGS. 3 and 4, it can be seen that the cam 56 and motor 58 arrangement is independently disposed on the frame 62 for engagement with the camming surfaces 64 and 66 of the primary transfer member 46. The cam 56 is spacially arranged between the two camming surfaces 64 and 66 for rotational engagement therewith. By engaging these camming surfaces 64 and 66, the cam 56 pivots the finger-like extension 50 of the primary transfer member 46 within the primary elongated aperture 42 of the workstation support surface 38. As it pivots, the finger-like extension 50 of the primary transfer member 46 engages an edge 43 of an opening 39 in the sample holder 35 to transfer the sample holder 35 a predetermined distance. Preferably, the predetermined distance is equivalent to the distance of one compartment, i.e., the distance between the centerline of one compartment and the centerline of an adjacent compartment, so that the primary transfer member 46 engages each of the openings 39 in the sample holder 35, advancing the sample holder 35 along the transfer path one compartment 37 at a time.

The cam 56 also pivots the finger like extension 50 of the primary transfer member 46 out of engagement with the edge 43 of the opening 39 to retract the primary transfer member 46 from the opening 39.

Preferably, the finger-like extension 50 is the portion of the primary transfer member 46 that pivots within the primary elongated aperture 42 for engagement with the sample holder 35, while the primary transfer block 48 pivots below the primary elongated aperture 42 and the associated workstation support surface 38.

As here embodied, and as seen in FIGS. 5-8, each cycle of the cam 56 along its rotational path corresponds to one cycle of the primary transfer member 46. Each cycle of the primary transfer member 46 includes a transfer portion of the cycle, shown in FIGS. 6 and 7, and a retracting portion of the primary transfer member cycle, shown in FIGS. 5 and 8. Referring to FIGS. 6 and 7, during the transfer portion of the primary transfer member cycle, the cam 56 engages the front block 64 for pivoting the primary transfer member 46 into engagement with the edge 43 of the opening 39 to transfer the sample holder 35 along the transfer path on the workstation support surface 38. Referring to FIG. 8, during the retracting portion of the primary transfer member cycle, the cam engages the rear block 66 for moving the primary transfer member 46 out of engagement with the edge 43 of the opening 39 to pivot the primary transfer member 46 and retract the primary transfer member from the opening 39.

Preferably, the front 64 and rear 66 blocks of the primary transfer member 46 are disposed substantially parallel to one another on the primary transfer block 48 and the cam 56 is arranged therebetween. By this arrangement, the cam 56 engages the inner facing walls of the front 64 and rear 66 blocks.

The following is a more detailed description of the phases of the primary transfer member cycle shown in FIGS. 5-8.

In FIG. 5, the primary transfer member 46 is fully retracted. Position A of the cam 56, shown in hard lines, reflects the beginning of a primary transfer member cycle. The cam 56 is positioned at the middle of the rear block 66 and the finger-like extension 50 is positioned at an extreme end of the primary elongated aperture 42, retracted from the sample holder 35. The cam 56 moves in a clockwise direction from position A to position B, shown in dashed lines in FIG. 5, without pivoting the primary transfer member 46. In position B, the cam 56 is at an upper portion of its rotational path, beginning to contact the front block 64. As the cam 56 engages the front block 64 in its clockwise rotation, the finger-like extension 50 begins to pivot within the primary elongated aperture 42 and toward an opening 39 of the sample holder 35.

In FIG. 6, as the cam 56 pushes against the front block 64 into position C, the primary transfer member 46 is pivoted upward, into engagement with the sample holder 35. Specifically, the finger-like extension 50 pivots into an opening 39 and engages an edge 43 of the opening 39 to move the sample holder 35 along the workstation support surface 38. The finger-like extension 50 may slightly engage the sample tube 41 arranged in the compartment 37 as it pivots into the opening 39. This movement is minimal, however, and does not misalign the sample tube 41 or otherwise upset its contents after filling.

In FIG. 7, position D shows the position of the cam 56 after having rotated clockwise down the length of the front block 64, thereby urging the primary transfer member 46 forward within the primary elongated aperture 42, as indicated by the arrow. During this forward movement of the primary transfer member 46, the finger like extension 50 engaged with the edge 43 of the opening 39 moves within the primary elongated aperture 42 to urge the sample holder 35 forward along the transfer path on the workstation support surface 38.

In FIG. 8, positions E and F of the cam 56 show the positions of cam 56 as it rotates clockwise away from engagement with the front block 64 (position E) and into engagement with a lower portion of the rear block 66 (position F). This movement causes the primary transfer member 46 to pivot backward, thereby pivoting the finger-like extension 50 backward within the primary elongated aperture 42 to retract the finger-like extension 50 from the sample holder 35. As the cam 56 rotates clockwise from position F, shown in FIG. 8, it moves along the surface of the rear block 66 until it returns to the beginning of the primary transfer member cycle, shown by position A in FIG. 5.

As here embodied, and as seen in FIGS. 1-4, the second transfer means includes secondary elongated apertures 68 spaced from the primary elongated aperture 42 on the workstation support surface 38. Moreover, the second transfer means includes secondary transfer members 70 movable within these secondary elongated apertures 68. In this way, the second transfer means can transfer a plurality of sample holders 35 to and from the workstations.

The secondary transfer members 70 are connected to the primary transfer member 46 for movement therewith by connecting means. Preferably, and referring to FIG. 3, the connecting means comprises a transfer shaft 72. Each of the primary 46 and secondary 70 transfer members are pivotally mounted on the transfer shaft 72. Preferably, the primary 46 and secondary 70 transfer members are pivotally fixed to the transfer shaft 72 by pin 74.

As here embodied, adjusting means are provided for adjusting the relative positions of the transfer members 46, 70. Preferably, the adjusting means include adjusting rods 76 arranged between adjacent transfer members 46, 70. As shown in FIG. 3, and in enlarged form in FIGS. 5-8, threads 78 are arranged at opposite ends 80 of the adjusting rods 76. Each threaded end 80 is received at a transfer member by an internally threaded sleeve 82. The ends 80 are threaded in opposite directions, one being left-hand threaded and the other end being right-hand threaded. The sleeves 82 are pivotally mounted to the transfer members 46, 70. Preferably, the sleeves 82 are pivotally fixed to the respective transfer members 46, 70 by pins 84.

By rotating the adjusting rods 76 having threaded ends 80 engaged with internally threaded sleeves 82, one may manually adjust the relative position of adjacent transfer members 46, 70. Rotating the rods 76 in one direction causes the adjacent transfer members 46, 70 to move closer together, whereas rotating the adjusting rods 76 in the opposite direction causes the adjacent transfer members 46, 70 to move further apart.

In accordance with the invention, control means are provided for coordinating the actuation of the first transfer means, the second transfer means and the workstations. As here embodied, and referring particularly to FIG. 2, the control means includes a first monitoring means 86 for monitoring the presence or absence of a sample holder 35 in the entrance area 45 of the workstation support surface 38. Preferably, the first monitoring means is a light emitting diode (LED) 86 for detecting the presence or absence of a sample holder 35 in the entrance area 45.

As here embodied, the control means also includes a first signal means 88 operatively connected to the first monitoring means 86 for actuating the second transfer means whenever the first monitoring means 86 indicates that a sample holder 35 is present in the entrance area 45.

As here embodied, the control means also includes a second signal means 90 operatively connected to the first monitoring means 86 for actuating the second transfer a predetermined number of times whenever the first monitoring means 86 indicates that a sample holder 35 is not present in the entrance area 45.

For example, the control means preferably includes a first counter associated with the first monitoring means for monitoring the number of transfers of the second transfer means while there are no sample holders 35 present in the entrance area 45 as indicated by the first monitoring means 86. When the first counter reaches a predetermined number, such as three, the second signal means actuates the first transfer to transfer an additional sample holder 35 into the entrance area 45.

In this way, by the first signal means 88, the second transfer means is actuated when a sample holder 35 is present in the entrance area 45 at the beginning of operation to clear away the pre-existing sample holder 35 from the entrance area 45 and transfer it to the exit support table 34. Additionally, by the second signal means 90, the second transfer means is still actuated for a predetermined number of times when a sample holder 35 is continuously not present. This actuation of the second transfer means when no sample holder 35 is present in the entrance area 45 provides a space between a sample holder 35 on the workstation support 38 and a sample holder 35 being transferred into the entrance area 45 of the workstation support 38 by the first transfer means.

Preferably, the predetermined amount of times that the second transfer means is actuated is three, which corresponds to three cycles of the primary transfer member 46, or moving the sample holder 35 leaving the entrance area 45 a distance equal to the length of three compartments 37. Thus, a space is provided between the sample holders 35 during transfer along the workstation support 38 to reduce the opportunity for contact between the adjacent sample holders 35.

As here embodied, the control means also includes third signal means 100 operatively connected to the first monitoring means 86 for actuating the first transfer means whenever a sample holder 35 is still not present in the entrance area 45 after the above predetermined number of actuations of the second transfer means by the second signal means 90.

Thus, by the above first monitoring means 86 and first, second, and third signal means, 88, 90, 100, the second transfer means is immediately actuated by the first 88 or second 90 signal means upon turning the machine on, whereby any existing sample holders 35 in the entrance area 45 of the workstation support 38 may be cleared from the entrance area 45 and transferred toward the exit support 34. Once any existing sample holder 35 has been cleared from the entrance area 45, however, and after a predetermined number of actuations of the second transfer means by the second signal means 90, the third signal means 100 actuates the first transfer means, thereby providing another sample holder 35 to the entrance area 45 of the workstation support 38. This monitoring system prevents contact between sample holders 35 in the entrance area 45 of the workstation support 38. Moreover, by permitting a spacing between the sample holders being transferred along the workstation support 38, any possible contact between the sample holders 35 is further prevented during transfer.

Referring to FIGS. 1 and 2, the control means also includes second monitoring means 92 for monitoring the presence of a sample holder 35 in an exit area 94 of the workstation support surface 38. Preferably, this second monitoring means 92 is a light emitting diode (LED) which monitors the presence or absence of a sample holder 35. Preferably, the second monitoring means 92 is arranged at an end position 96 of the transfer path on the workstation support 38 for indicating when a sample holder 35 has reached the end position 96 of the workstation support surface 38.

Figure 13:
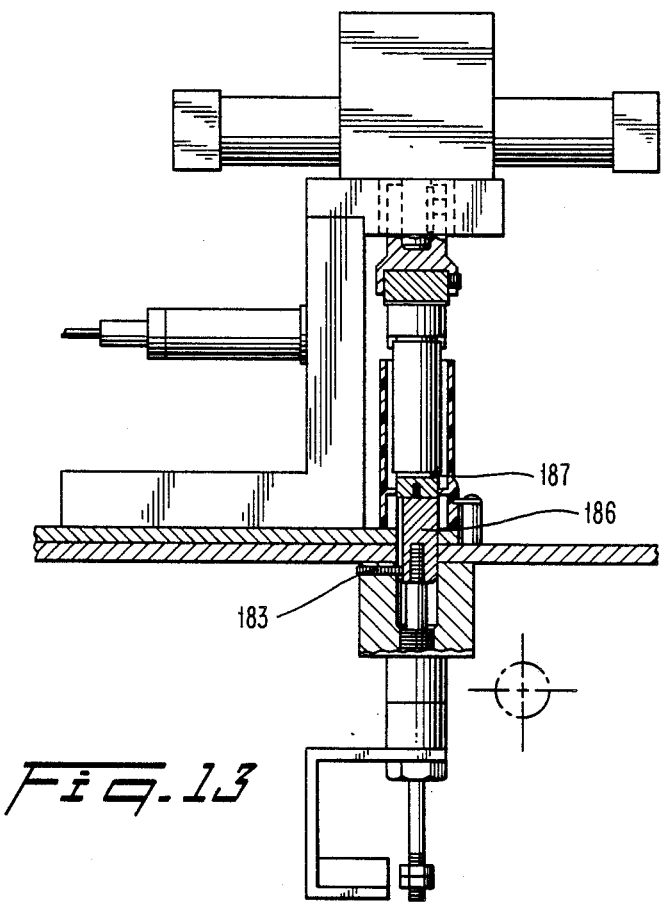
FIG. 13 is a side view of the tightening workstation shown in FIG. 12.

Referring to FIGS. 2, 13 and 14, the transfer device also includes third transfer means 98 disposed along the exit area 94 of the workstation support 38. The third transfer means 98 transfers sample holders 35 out of the exit area 94 of the workstation support 38 and into the exit support 34.

As here embodied, the control means further includes a fourth signal means 102 operatively connected to the second monitoring means 92 for actuating the third transfer means 98 whenever a sample holder 35 is present in the end position 96 of the exit area 94 of the workstation support 38.

Figure 10:
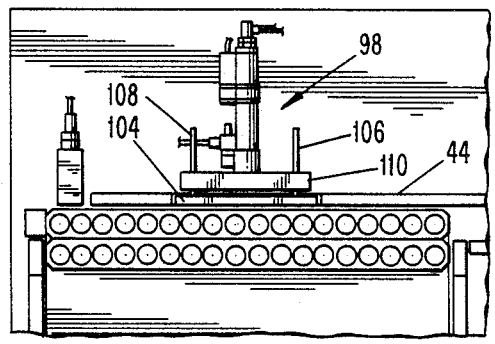
FIG. 10 is a top view of an exit area of the invention.
Figure 11:
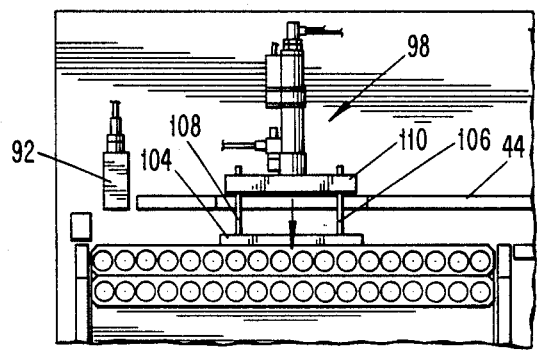
FIG. 11 is a top view similar to FIG. 10 and showing the exit transfer pushing a sample holder into an exit support.

Referring to FIGS. 2, 10 and 11, the third transfer means 98 preferably includes a pneumatically driven piston-like rail portion 104 which, in its non-actuated condition, is aligned with the guide rail 44 for guiding a sample holder 35 along the transfer path during transfer by the second transfer means. Sliding shafts 106, 108 are fixed at one end to the rail portion 104 of the third transfer means 98. In operation, and as shown specifically in FIG. 11, these shafts 106, 108 slide within apertures in a bearing block 110. Thus, in its actuated condition, the rail portion 104 is slidably movable across the workstation support 38 for engaging a side of the sample holder 35 and pushing the sample holder 35 out of the exit area 94 of the workstation support surface 38 and into the exit support table 34. Preferably, the rail portion 104 is a rectangularly shaped block which engages the sample holder 35 at a low area of the holder to prevent tipping of the sample holder 35 during transfer into the exit support table 34.

The third transfer means 98 arrangement highlights the usefulness of the spacing between the sample holders transferred by the first transfer. That is, a small amount of time is needed for the third transfer means 98 to respond to the fourth signal means by transferring a sample holder 35 to the exit support table 34, and to return to its original position shown in FIG. 10, before another sample holder 35 may be transferred into the exit area 94 of the workstation support surface 38.

As here embodied, a fifth signal means 112 is operatively connected to the second monitoring means 92 for de-actuating the second transfer means whenever a sample holder 35 is continuously not present in the end position 96 of the exit area 94 of the workstation support 38 for a predetermined number of transfer cycles of the second transfer means. Preferably, this predetermined number of transfer cycles is equivalent to the number of transfers required to move a sample holder 35 from a first position in the entrance area 45 of the workstation support surface 38 prior to transfer to the end position 96 in the exit area 94 of the workstation support 38. Only after this particular number of transfers could there be the assurance that no further sample holders 35 are available for transfer.

In accordance with the invention, the transfer device includes a plurality of workstations disposed along the workstation support surface 38 for interaction with the sample holders 35 transferred along the workstation support by the second transfer means. Each of the workstations performs a particular function with respect to the sample tubes 41 in the sample holders 35.

As here embodied, workstation monitoring means, generally designated 114, are associated with each of the plurality of workstations for monitoring the presence and absence of sample tubes 41 after each transfer of the second transfer means. The workstation monitoring means 114 are supportably arranged on various vertical extensions of the support frame 62. The workstation monitoring means 114 are arranged along the workstation support 38 to monitor the position of a sample tube 41 with respect to the workstations. Each time the second transfer transfers the sample holder 35, the particular workstation monitoring means will detect whether there is a sample tube 41 present at the workstation and whether it is properly aligned with respect to the workstation.

As here embodied, workstation signal means are associated with each of the workstation monitoring means 114 for actuating the particular workstation whenever the workstation monitoring means 114 indicates that a sample tube 41 is present and aligned at the workstation. If a sample tube 41 is not present at a workstation, the workstation signal means does not actuate the particular workstation. Thus, the workstation monitoring means and workstation signal means prevent the operation of the workstation if a sample tube 41 is not present in a particular compartment 37 of the sample holder 35.

Figure 12:
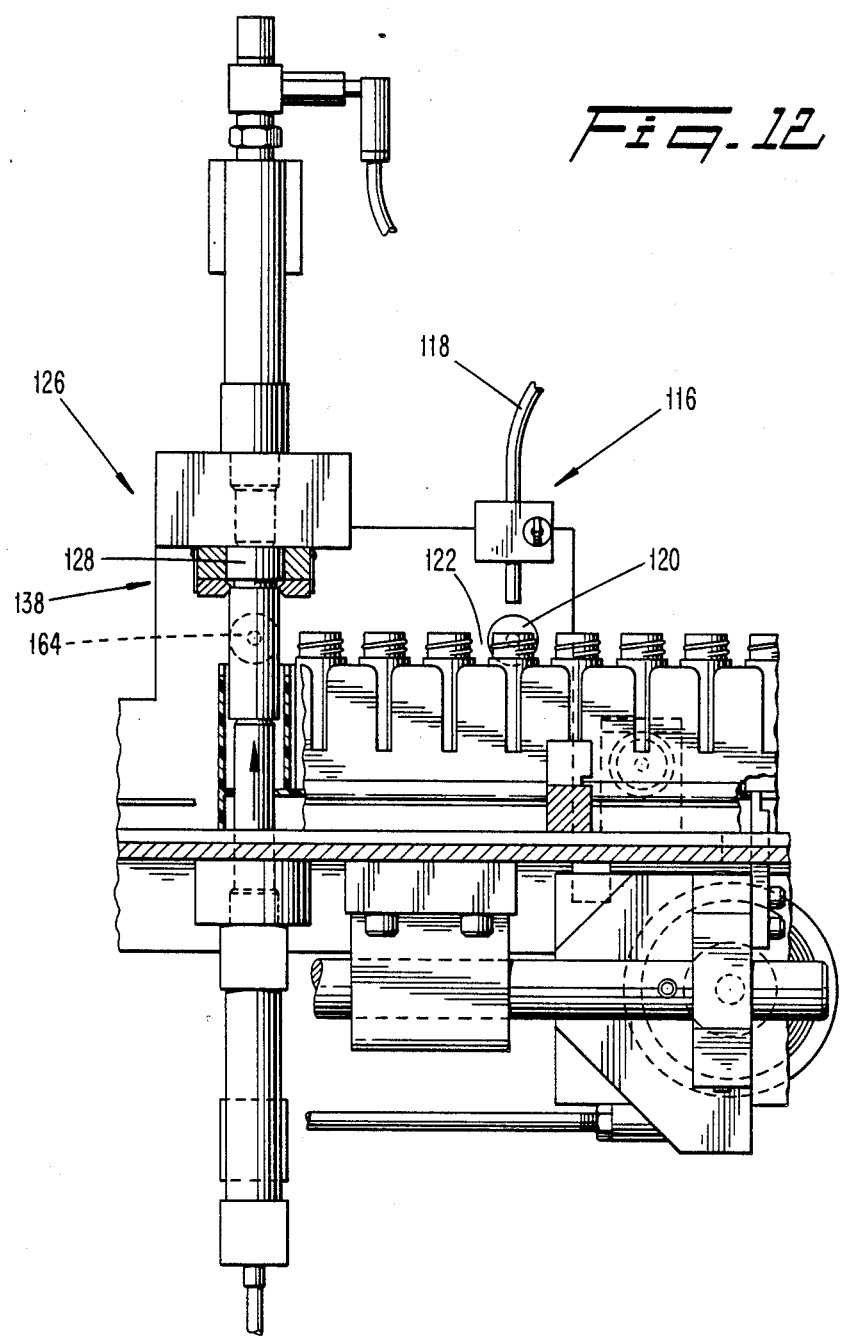
FIG. 12 is an enlarged front view of the filling workstation and capping workstation shown in FIG. 1.

As here embodied, and referring to FIGS. 1 and 12, one of the plurality of workstations is a filling workstation 116 for filling each of the sample tubes 41 in the sample holder 35 with a substance. As previously described, the filling workstation 116, as well as the other workstations, is operative during the retracting portion of the primary transfer member cycle, so that the sample holder 35 is not in motion during the filling process.

Preferably, the filling workstation 116 includes a substance container (not shown) which contains a quantity of the substance to be deposited in the sample tubes 41 and a dispensing tube 118 for dispensing a predetermined amount of the substance from the substance container to the individual sample tubes 41. This predetermined amount may vary depending on the size of the sample tubes 41 used. For example, in one application, the dispensing tube 118 dispenses 5 cc of liquid substance into each sample tube 41. A pump (not shown) delivers the predetermined amount of the substance from the substance container into the dispensing tube 118 for each actuation of the filling workstation.

A filling workstation monitoring means 120 is arranged to detect the presence of a sample tube at the filling workstation. A filling workstation signal means 124 is operatively connected to the filling workstation monitoring means 120 for actuating the workstation.

Preferably, the filling workstation monitoring means is a fiber optic light emitting diode (LED) 120 which can detect not only the presence of an object such as a sample tube 41, as is the case with a standard LED, but which can also detect the space 122 between the sample tubes 41. This additional feature of the fiber optic LED is important in preventing the double filling of a single sample tube 41.

For example, in the event of a failure of the second transfer means to transfer a filled sample tube 41 away from the filling workstation 116 and place an unfilled sample tube 41 under the filling workstation 116, a standard LED would still actuate the filling workstation 116, since it would indicate that a tube was present which should be filled by the filling workstation 116. However, with the fiber optic LED, the filling workstation 116 will not be actuated until the filling workstation monitoring means 120 indicates that there has been a successful transfer and that an unfilled sample tube 41 is present below the dispensing tube 118. That is, the filling workstation monitoring means 120 must go out, detecting a space 122 between the sample tubes, and go on again, detecting the presence of another sample tube 41, before the filling workstation signal means 124 will actuate the filling workstation 116. Thus, the more sensitive fiber optic LED used as the filling workstation monitoring means 120 provides a safety precaution against the double filling of a single sample tube and the resulting possibility of spillage.

As here embodied, and as shown in FIGS. 1, 2 and 12, another workstation includes a capping workstation 126 for placing a cap 128 on each of the sample tubes 41 as the tubes are transferred by the second transfer means to and from the capping workstation 126. Again, the capping operation is performed during the retracting portion of the primary transfer member cycle so that the sample holder 35 is still. As shown in FIG. 2, the capping workstation includes a cap supply means which includes a vibrational cap supply bowl 130. Through vibration, the cap supply bowl 130 moves caps 128 up a spiral ramp 132 on the outer periphery of the cap supply bowl 130 toward a cap guide 134 extending from the top 136 of the cap supply bowl 130 toward the portion 138 of the capping workstation 126 where the sample tubes 41 are capped.

As embodied herein, projections 140, 142 are provided along the ramp 132 for pushing off the ramp 132 any caps 128 stacked on top of one another, so that only a single row of non-stacked caps are delivered to the cap guide 134. As embodied herein, a sloped surface 144 is also provided along the ramp 132 for causing caps 128 that are incorrectly oriented to slide back into the cap supply bowl 130. Preferably, the desired orientation of the caps 128 is upside-down with the flat, closed surface of the cap 128 in contact with the ramp 132. The sloped surface 144 causes caps 128 oriented with the open side contacting the ramp 132 to slide down the ramp 132 and back into the cap supply bowl 130.

After the caps travel all the way up the ramp 132 to the top of the supply bowl 130, the caps 128 then continue toward a cap guide 134 which transports caps 128 via gravity from the top 136 of the cap supply bowl 130 to the capping portion 138 of the capping workstation 126. Due to the spiral configuration of the cap guide 134, the caps 128 are rotated so as to be in an upright position at the cap guide exit 146. At the cap guide exit 146, the cap guide 134 deposits the caps 128 individually into a cap retaining area 148 that is aligned with the sample tube 41 transferred to the capping workstation 126.

Referring to FIGS. 14-17, the cap retaining area 148 includes a block 150 with a hollow portion 152 for receiving the cap 128 from the cap guide 134 and surrounding the sides of the cap 128. Levers 154 are pinned to the block 150 for pivoting on a horizontal plane just below the cap 128. Specifically refer ring to FIG. 17, the levers 154 are biased inward in the position shown in solid lines. The dashed lines show the position of the levers 154 when they are pushed outward in a direction shown by the arrows in FIG. 17. In the relaxed position, with the levers 154 biased inward, the levers 154 support the bottom of the cap 128 in the cap retaining area 148. The levers each have a semicircular cut-out portion 156 for exposing part of the bottom portion of the cap while the cap 128 is in the cap retaining area 148. This semicircular cut-out portion 156 of the levers 154, shown in a top view in FIG. 17, has a sloped cross-section, as shown in FIGS. 14-16. The center 158 of the cross-section of the cut-out portions 156 extends further than the upper 160 or lower 162 portions of the cut-out portion 156. This sloped surface creates a narrower aperture between the centers 158 of the semicircular cut-out portions 156 of the levers 154 than at the upper 160 and lower 162 areas of the semicircular cut-out portions 156.

As here embodied, and referring to FIG. 2, the control means further comprises capping workstation monitoring means 164 for monitoring the presence of a sample tube 41 at the capping workstation 126. Moreover, capping workstation signal means 166 operatively connected to the capping workstation monitoring means 164 are provided for actuating the capping workstation 126 whenever a sample tube 41 is present at the capping workstation 126, as indicated by the capping workstation monitoring means 164.

In operation, and referring to FIGS. 14-17, a cap 128 is deposited into the cap retaining area 148 and suspended above a sample tube 41 transferred to the capping workstation 126. The cap 128 is held in suspension by the levers 154 which supportably engage the bottom of the cap at the sloped upper surfaces 160 of the semicircular cut-outs 156. When the capping workstation monitoring means 164 indicates that a sample tube 41 is present in the particular compartment 37 of the sample holder 35 transferred to the capping workstation 126, the capping workstation signal means 166 activates the capping workstation 126.

As shown in FIG. 17, elevating means are provided for elevating the sample tube 41 out of the compartment 37 and toward the cap retaining area 148. Referring to FIG. 14, the elevating means includes an elevator 168 having an elevating rod 170 arranged below the workstation support surface 38. The elevating rod 170 is movable through a hole 172 in the workstation support 38 and the opening 39 in the sample holder 35 for engaging a sample tube 41 and lifting the sample tube out of its compartment 37 and toward the cap retaining area 148 of the capping workstation 126. The force of the elevating rod 170 pushes the threaded top 174 of the sample tube 41 along the lower sloped portion 162 of the semicircular cut-out portion 156 of the levers 154. As the threaded top 174 of the sample tube is urged upward, along the lower sloped portion 162 and center 158 of the semicircular cut-out portion 156, it pushes the levers 154 outward as shown in dashed lines in FIG. 17, clearing an entrance into the cap 128 for the threaded top 174 of the sample tube 41.

The force of the elevating rod 170 pushes the threaded top 174 into the threaded cap 128 so that at least some of the threads on the cap 128 and tube 41 engage one another. Referring to FIG. 15, the elevating rod 170 then retracts.

The capping workstation 126 also includes releasing means for releasing the capped sample tube from engagement with the levers and depositing the sample tube back into its compartment. As shown in FIG. 16, the releasing means is preferably a downwardly moving punching device 176 having a punching rod 178 arranged directly above the cap retaining area 148 for downwardly engaging the top of the cap 128 and pushing the capped sample tube back into its compartment 37. The downward movement of the punching rod 178 pushes the cap against the sloped semicircular cut-out portions 156 of the levers 154 to urge them outward. This downward movement occurs substantially simultaneously with the retracting of the elevating rod 170.

As here embodied, and as seen in FIGS. 1, 2, and 18–20, another of the plurality of workstations includes a tightening workstation for tightening the caps placed on the sample tubes at the capping workstation. The tightening workstation 180 includes rotating shaft means having frictional means arranged thereon for engaging the top of a cap on a sample tube. The rotatable shaft means includes a rotatable shaft element 182 aligned with the top of the cap 128 to be tightened. The frictional means includes a frictional material 184 arranged on the end of the rotating shaft 182.

Tightening workstation monitoring means are provided for detecting a sample tube 41 at this lifted position. Preferably, the tightening workstation monitoring means 188 is an LED. Tightening workstation signal means 190 operatively connected to the tightening workstation monitoring means 188 are provided for actuating the tightening workstation 180.

Figure 19:
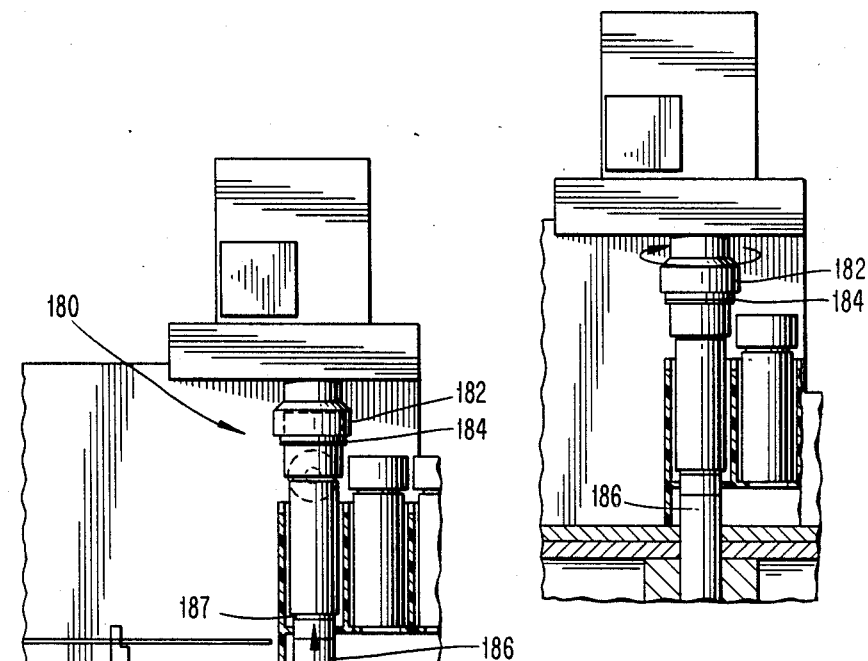
FIG. 19 is a view similar to FIG. 18 and shows a sample tube being tightened at the tightening workstation.
Figure 20:
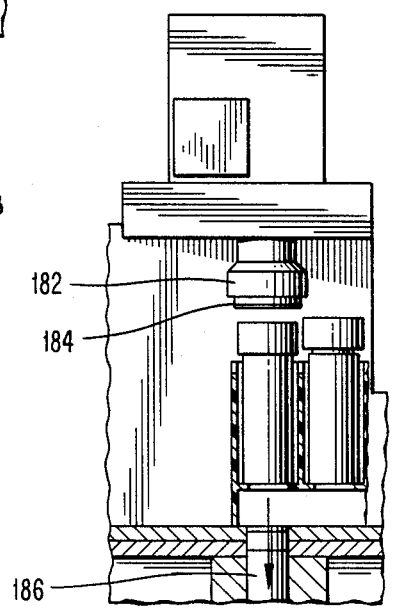
FIG. 20 is a view similar to FIG. 18 and shows the tightened sample tube after release from the tightening workstation.

As shown in FIGS. 13, and 18–20, in operation, the individual sample tubes 41 are lifted by an elevator 186 having a frictional material 187 toward the rotatable shaft element 182 with the frictional material 184 attached at a flat end surface thereof. Referring to FIG. 19, the cap 128 engages the frictional material 184 of the rotatable element 182, whereby the rotatable shaft element 182 is rotated to tighten the cap 128 on the individual tube 41. An anti-rotate pin 183 (FIG. 13) is provided to prevent the elevating rod 186 from rotating during the tightening of the cap. The elevator 186 is then moved downward and the tightened cap and tube are replaced in its compartment 37, as shown in FIG. 20. Preferably, the frictional materials 184 and 187 are a rubber material.

As here embodied, another of the plurality of workstations includes a labeling workstation for labeling each of the sample tubes.

The labeling workstation 192 includes labeling means for labeling a sample tube and positioning means for positioning the sample tube for labeling. As here embodied, and referring to FIGS. 2 and 21, the labeling means includes an ink jet printer head 194 moveably positioned on a shaft 196 arranged perpendicularly to the transfer path of the sample holders 35 for traversing across the top of the capped tubes 41. The positioning means includes elevating means for elevating individual sample tubes 41 toward the ink jet printer head 194 and a stop 200 for defining an end position of the elevated sample tube 41. The elevating means includes an elevating rod 202 arranged directly below a sample tube 41 at the labeling workstation for moving through the workstation support surface 38 and the opening 29 in the compartment 37 of the sample holder 35. The elevating rod 202 engages and lifts the bottom of the sample tube 41 until the cap engages the stop 200. The stop 200 is positioned to engage only a portion of the cap 128, leaving a portion of the cap 128 exposed for receiving the printer head 194.

As here embodied, labeling workstation monitoring means 204 are provided for monitoring the presence or absence of a sample tube 41 at the labeling workstation 192. Labeling workstation signal means 206 are also provided for actuating the labeling workstation 192 whenever the labeling workstation monitoring means 204 indicates that a sample tube 41 is present.

Figure 21:
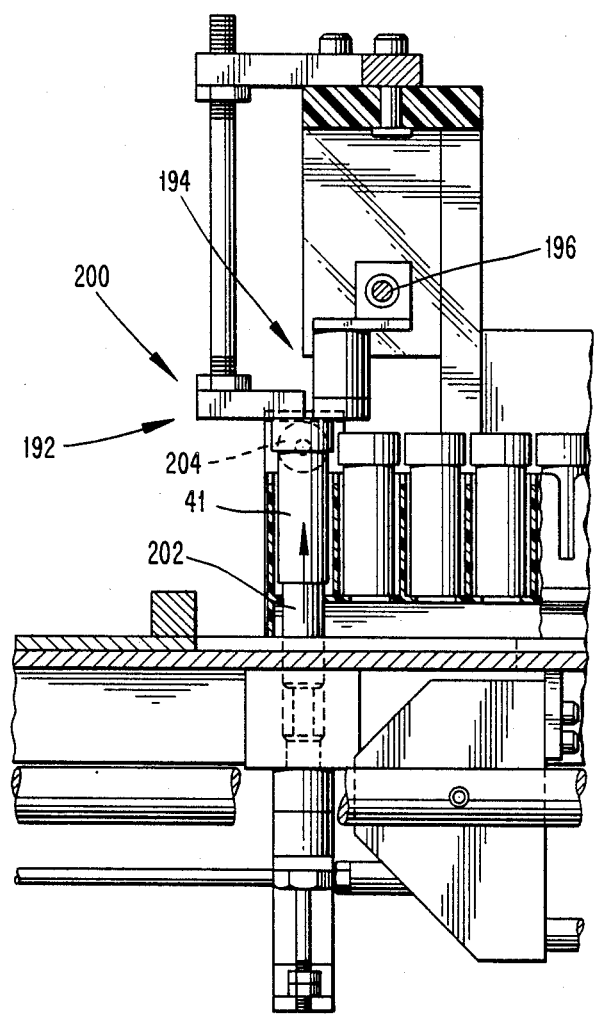
FIG. 21 is an enlarged view of the labeling workstation shown in FIG. 1.

As shown in FIG. 21, in operation the sample tube 41 is lifted by the elevator rod 202 against an end stop 200, whereby the reciprocating printing head 194 traverses the exposed top of the cap 128 for printing a label on the cap 128. The elevating rod 202 then brings the labeled tube 26 down back into its compartment 37 in the sample holder 35 and the printing head 194 traverses back to its original position for labeling the next sample tube.

In operation, the device according to the invention operates as follows. An operator loads a predetermined number of sample holders 35 onto an entrance support table 30. The apparatus is then turned on by a switch (not shown) attached to a controller (not shown). The second transfer means, including primary transfer member 46 and secondary transfer member 70 attempts to transfer any sample holders 35 present in the workstation support entrance area 45 by transferring the primary and secondary transfer members a predetermined number of times. Preferably, one of the primary 46 or secondary transfer members 70 are located along the entrance area 45 of the workstation support surface 38.

Once the apparatus is on, the first signal means 88 responsive to the first monitoring means 86 actuates the second transfer means. As long as the first monitoring means indicates that a sample holder 35 is present in the entrance area, the second transfer means will continue to transfer the sample holder 35 along the workstation support surface 38. If the first monitoring means 86 reflects that no sample holder 35 is present in the entrance area 45, the second signal means 90 actuates the second transfer means a predetermined number of times. After the second transfer means is actuated a predetermined number of times, and the first monitoring means 86 indicates that no sample holder 35 is present, a third signal means 100 operatively connected to the first monitoring means 86 actuates the first transfer means.

The endless belts 47, 47a of the first transfer means move the sample holders 35 deposited in the entrance support table 30 toward the entrance area 45 of the workstation support surface 38, depositing one of the sample holders 35 into the entrance area 45, as shown in FIG. 1. The presence of the sample holder 35 in the entrance area is detected by the first monitoring means 86 which triggers a first signal means 88 for actuating the second transfer means and for de-actuating the first transfer means. This process will continue until all of the sample holders 35 from the entrance support table 30 have been transferred into the entrance area 45 of the workstation support surface 38.

As the sample holders 35 move along the workstation support surface 38, they move to a first workstation, which is the filling workstation 116. The filling workstation monitoring means 120 indicates that a sample tube 41 is present and the filling workstation signal means 124 actuates the filling workstation 116. The pump and substance container of the filling workstation 116 then deposit a predetermined amount of the sample substance through a dispensing tube 118 into the sample tube 41. As this filling step occurs, the second transfer means is in the retracting portion of its transfer cycle, so that the sample holders 35 are not moving during the filling step.

The filled sample tubes 41 then move on to the second workstation, which is the capping workstation 126. As shown in FIGS. 14-17, the individual sample tubes 41 are raised by an elevator rod 170 disposed under the capping workstation 126 toward the cap retaining area 148 where the sample tube is pushed into a cap 128 suspended in the cap retaining area 148 by retaining levers 154. As the sample tube 26 is pushed into the cap 128, the retaining levers 154 engage the sample tube just below the bottom edge of the cap. The elevator rod 170 then moves downward (FIG. 15) and simultaneously, a downwardly moving punching rod 178 pushes the capped sample tube 41 out of the cap retaining area 148 (FIG. 16), urging the retaining levers 154 outward and pushing the capped tube 41 downward into its corresponding compartment 37. The pivoting action of the levers 154, and a top view of the semicircular cut-out 156 portion of the levers 154, are shown in detail in FIG. 17.

Again, at the capping workstation 126, as at all of the workstations, during operation of the workstation the second transfer means is in the retracting portion of the transfer cycle so that the sample holders 35 and tubes 41 are still during operation of the workstation. Additionally, a capping workstation monitoring means 164 shown in FIG. 12, monitors the presence or absence of a sample tube 41 at the capping workstation 126 and a capping workstation signal means 166 actuates the capping workstation only when a tube 41 is present at the capping workstation 126.

Figure 18:
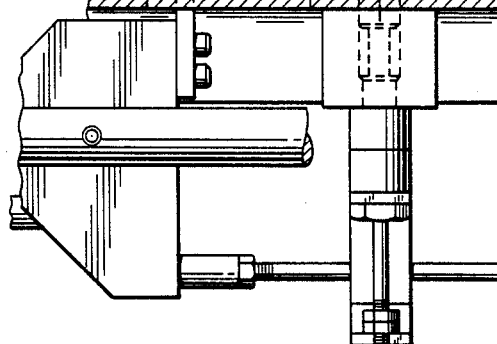
FIG. 18 is an enlarged front view of the cap tightening workstation shown in FIG. 1.

The capped tubes 41 are then transferred to a third workstation, which is a cap tightening workstation 180. The tightening workstation monitoring means 188, shown in FIG. 18, detects the presence of a sample tube 41 and the tightening workstation signal means 190 operatively connected to the tightening workstation monitoring means 188 actuates the tightening workstation 180. As shown in FIGS. 18-20, the capped sample tube 41 is lifted by an elevator rod 186 having a frictional material 184 out of its compartment 37 toward a rotatable shaft element 182 having a friction material 184 attached to the end thereof. As the capped tube 41 engages the friction material 184 on the shaft, the shaft 182 rotates, thereby tightening the cap 128 onto the tube 41, as shown in FIG. 19. The elevator rod 186 then lowers the tightened capped tube back into its corresponding compartment 37 of the sample holder 35.

The tightened capped tubes 41 are then transferred toward a fourth workstation, which is a labeling workstation 192. The labeling workstation monitoring means 204 detects the presence or absence of a capped tube 41 and the labeling workstation signal means 206 actuates the labeling workstation 192 whenever a tube 41 is present at the workstation. As shown in FIG. 21, an elevator rod 202 lifts the capped tube 41 upward against the stop 200. A reciprocating print head 194 movable along a shaft 196 travels across the top of the cap 128 and prints a label on the cap 128. The elevator rod 202 then lowers the labeled tube back into the compartment 37, while the reciprocating head 194 returns to its original position.

As shown in FIGS. 10 and 11, when the sample holder 35 moves into an end position 96 in the exit area 97 of the workstation support surface 38, a second monitoring means 92 detects the presence of the sample holder 35 and the fourth signal means 102 actuates the third transfer to move the sample holder onto the exit support table 34. The third transfer means includes a rail portion 104 integral with the guide rail 44 along the workstation support 38, which rail portion 104 moves across the exit area 97 of the workstation support surface 38 to push the sample holder 35 from the exit area 97 of the workstation support surface 38 and into the exit support table 34, as shown in FIG. 11.

Other embodiments of the invention will be apparent to the skilled in the art from consideration of the specification and practice of the invention disclosed herein. It is intended that the specification and examples be considered as exemplary only, with a true scope and spirit of the invention being indicated by the following claims.

What is claimed is:

1. A device for transferring sample tubes arranged in elongated sample holders to and from consecutive workstations positioned along a transfer path, comprising:

entrance support means for supplying said sample holders to said transfer path;

exit support means for receiving said sample holders from said transfer path;

workstation support means extending between said entrance support means and said exit support means for supporting said sample holder during transfer to and from said workstations, said workstation support means defining an entrance area for receiving said sample holders from said entrance support means;

guide means disposed along said workstation support means for guiding said sample holders within said workstation support means toward said exit support means;

first transfer means disposed along said entrance support means for transferring each of said sample holders individually into said entrance area of said workstation support means;

second transfer means disposed along said workstation support means for engaging said sample holders to transfer said sample holders a predetermined amount along said workstation support means;

control means for coordinating actuation of said first transfer means, said second transfer means and said workstations to ensure smooth operation of said device, said control means including first monitoring means for monitoring the presence of a sample holder in said entrance area, first signal means operatively connected to said first monitoring means for actuating said second transfer means when a sample holder is present in said entrance area; and second signal means operatively connected to said first monitoring means for actuating said second transfer means a first predetermined number of times when a sample holder is not present in said entrance area.

2. The device of claim 1, said control means including:
third signal means operatively connected to said first monitoring means for actuating said first transfer means when a sample holder is continuously not present in said entrance area after said second transfer means is actuated said first predetermined number of times.

3. The device of claim 2, wherein said workstation support means defines an exit area for receiving said sample holders after transfer by said second transfer means along said workstation support means, and wherein said transfer device further comprises third transfer means disposed along said exit area for transferring said sample holders individually from said exit area to said exit support means.

4. The device of claim 3, said control means further including:
second monitoring means for monitoring the presence of a sample holder in said exit area of said workstation support means; and
fourth signal means operatively connected to said second monitoring means for actuating said third transfer means when a sample holder is present in said exit area of said workstation support means.

5. The device of claim 4, said control means further including fifth signal means operatively connected to said second monitoring means for de-actuating said second transfer means when a sample holder is continuously not present in said exit area after said second transfer means is actuated a second predetermined number of times.

6. The device of claim 5, further comprising a plurality of workstations disposed along said workstation support means;
workstation monitoring means associated with each of said plurality of workstations for monitoring the presence of sample tubes at each of said plurality of workstations; and
workstation signal means operatively connected to each of said workstation monitoring means for actuating a corresponding workstation when a sample tube is present.

7. The device of claim 6, wherein one of said plurality of workstations includes a filling workstation for filling each of said sample tubes with a substance when said sample tubes are transferred to said filling workstation.

8. The device of claim 7, wherein another of said plurality of workstations includes a capping workstation for placing a cap on each of said sample tubes when said sample tubes are transferred to said capping workstation.

9. The device of claim 8, wherein another of said plurality of workstations includes a tightening workstation for tightening said caps placed on said sample tubes at said capping workstation when each of said sample tubes is transferred to said tightening workstation.

10. The device of claim 9, wherein another of said plurality of workstations includes a labelling workstation for labelling said sample tubes as said sample tubes are transferred to said labelling workstation.

11. The device of claim 10, wherein said workstation support means includes a primary elongated aperture, and wherein said second transfer means includes a primary transfer member pivotally mounted to pivot within said primary elongated aperture and to engage said sample holders.

12. The device of claim 11, wherein said sample holder includes a row of compartments for individually supporting sample tubes disposed therein, each of said compartments having an opening along a bottom surface of said sample holder, said opening having a smaller diameter than said sample tube, said primary transfer member being pivotable within said opening to engage an edge thereof for transferring said sample holder along said transfer path.

13. The device of claim 12, wherein said transfer means includes cam means for pivoting said primary transfer member within said primary elongated aperture and into engagement with said sample holder and for pivoting said primary transfer member out of engagement with said sample holder, wherein said pivoting into and out of engagement with said sample holders constitutes one primary transfer member cycle, said pivoting into engagement with said sample holder being a transfer portion of said primary transfer member cycle for transferring said sample holder along said transfer path and said pivoting out of engagement with said sample holder being a retracting portion of said primary transfer member cycle for maintaining said sample holder in a stationary position on said transfer path.

14. The device of claim 13, wherein said cam means includes camming surfaces disposed on said primary transfer member and a cam moveably disposed for engagement with said camming surfaces for pivoting said primary transfer member.

15. The device of claim 14, wherein said second transfer means includes driving means for rotating said cam, each rotation of said cam being timed to correspond to the cyclical pivoting of said primary transfer member, thereby urging said primary transfer member into and out of engagement with said sample holder during each cycle of said cam.

16. The device of claim 15, wherein said workstation signal means operatively connected to each of said workstation monitoring means are operative for actuating said workstations during said retracting portion of said primary transfer member cycle when said sample holder is in a stationary position on said transfer path.

17. The device of claim 16, wherein said camming surface on said primary transfer member includes a forward block and a rear block spaced from said forward block, and wherein during said transfer portion of said primary transfer member cycle said cam engages said forward block for pivoting said primary transfer member into engagement with said edge of said opening and wherein during said retracting portion of said primary transfer member cycle said cam engages said rear block for pivoting said primary transfer member out of engagement with said edge of said opening.

18. The device of claim 17, wherein said workstation sup port means includes secondary elongated apertures spaced from said primary elongated aperture, and wherein said second transfer means includes secondary transfer members moveable within corresponding ones of said secondary elongated apertures for transferring additional sample holders along said transfer path, said second transfer means further including connecting means for connecting said secondary transfer members with said primary transfer member for movement therewith.

19. The device of claim 18, wherein said connecting means includes a transfer shaft, each of said primary and secondary members being pivotally mounted on said transfer shaft.

20. The device of claim 19, wherein said transfer means further includes adjusting means disposed between adjacent ones of said primary and secondary transfer members for adjustably positioning said primary and secondary transfer members.

21. The device of claim 20, wherein said adjusting means includes an adjusting rod threaded at opposite ends thereof and receiving means disposed on said adjacent ones of said primary and secondary transfer members for threadedly receiving said threaded ends, said adjusting rod being substantially parallel to said transfer shaft.

22. The device of claim 21, wherein said forward and rear blocks are substantially parallel, each of said forward and rear blocks having an inner facing wall, said cam being moveably disposed for sequential engagement with said inner facing walls of said forward and rear blocks.

23. The device of claim 22, wherein said primary and secondary transfer members transfer said sample holders a predetermined distance along said transfer path during each cycle thereof, said predetermined distance being equivalent to the length of one compartment so that said primary and secondary transfer members engage each of the openings in said sample holders for advancing said sample holders along said transfer path one compartment at a time.

24. The device of claim 23, wherein each of said primary and secondary transfer members includes a finger-like extension for pivoting within corresponding ones of said primary and secondary elongated apertures and in and out of engagement with said sample holders during said primary transfer member cycle.

25. The device of claim 7, wherein said filling workstation includes:
substance container means for containing a quantity of said substance; and
dispensing means for dispensing a predetermined amount of said sample substance into one of said sample tubes for each actuation of said filling workstation by said filling workstation signal means.

26. The device of claim 8, wherein said capping workstation includes:
cap supply means for supplying said caps;
cap guide means for guiding said caps from said cap supply means into a cap retaining area;
elevator means for raising each sample tube toward said cap retaining area for urging said sample tube into engagement with a cap in said retaining area; and
lever means for engaging said sample tube as said sample tube engages said cap and for releasing said sample tube to return said sample tube to its corresponding compartment.

27. The device of claim 9, wherein said tightening workstation includes a rotatable shaft element having a frictional element arranged at an end portion thereof for engaging said cap and rotating said cap to tighten the cap onto the sample tube.

28. A device for transferring sample tubes arranged in elongated sample holders to and from a plurality of consecutive workstations positioned along a transfer path, comprising:
entrance support means for supplying said sample holders to said transfer path;
exit support means for receiving said sample holders from said transfer path;
workstation support means extending between said entrance support means and said exit support means for supporting said sample holder during transfer to and from each of said plurality of workstations, said workstation support means defining an entrance area for receiving said sample holders from said entrance support means;
workstation monitoring means associated with each of said plurality of workstations for monitoring the presence of sample tubes at each of said plurality of workstations;
workstation signals means operatively connected to each of said workstation monitoring means for actuating a corresponding workstation when a sample tube is present;
guide means disposed along said workstation support means for guiding said sample holders within said workstation support means toward said exit support means;
first transfer means disposed along said entrance support means for transferring each of said sample holders individually into said entrance area of said workstation support means;
second transfer means disposed along said workstation support means for engaging said sample holders to transfer said sample holders a predetermined amount along said workstation support means; and
control means for coordinating actuation of said first transfer means, said second transfer means and said workstations to ensure smooth operation of said device, said control means including first monitoring means for monitoring the presence of a sample holder in said entrance area, and first signal means operatively connected to said first monitoring means for actuating said second transfer means when a sample holder is present in said entrance area.

29. The device of claim 28, wherein said workstation support means defines an exit area for receiving the sample holders after transfer by said second transfer means along said workstation support means, and wherein said transfer device further comprises third transfer means disposed along said exit area for transferring said sample holders individually from said exit area to said exit support means.

30. The device of claim 29, wherein said workstation support means includes a primary elongated aperture, and wherein said second transfer means includes a primary transfer member pivotally mounted to pivot within said primary elongated aperture and to engage said sample holders.

31. The device of claim 29, wherein said sample holder includes a row of compartments for individually supporting sample tubes disposed therein, each of said compartments having an opening along a bottom surface of said sample holder, said opening having a smaller diameter than said sample tube, said primary transfer member being pivotable within said opening to engage an edge thereof for transferring said sample holder along said transfer path.

32. The device of claim 31, wherein said second transfer means includes cam means for pivoting said primary transfer member within said primary elongated aperture and into engagement with said sample holder and for pivoting said primary transfer member out of engagement with said sample holder, wherein said pivoting into and out of engagement with said sample holders constitutes one primary transfer member cycle, said pivoting into engagement with said sample holder being a transfer portion of said primary transfer member cycle for transferring said sample holder along said transfer path and said pivoting out of engagement with said sample holder being a retracting portion of said primary transfer member cycle for maintaining said sample holder in a stationary position on said transfer path.

33. The device of claim 32, wherein said cam means includes a camming surface disposed on said primary transfer member and a cam moveably disposed for engagement with said camming surface for pivoting said primary transfer member.

34. The device of claim 33, wherein said second transfer means includes driving means for rotating said cam, each rotation of said cam being timed to correspond to the cyclical pivoting of said primary transfer member, thereby urging said primary transfer member into and out of engagement with said sample holder during each cycle of said cam.

35. The device of claim 34, wherein said workstation signal means operatively connected to each of said workstation monitoring means are operative for actuating said workstations during said retracting portion of said primary transfer member cycle when said sample holder is in a stationary position on said transfer path.

36. The device of claim 35, wherein said camming surface on said primary transfer member includes a forward block and a rear block spaced from said forward block, and wherein during said transfer portion of said primary transfer member cycle said cam engages said forward block for pivoting said primary transfer member into engagement with said edge of said opening and wherein during said retracting portion of said primary transfer member cycle said cam engages said rear block for pivoting said primary transfer member out of engagement with said edge of said opening.

37. The device of claim 36, wherein said workstation support means includes secondary elongated apertures spaced from said primary elongated aperture, and wherein said second transfer means includes secondary transfer members moveable within corresponding ones of said secondary elongated apertures for transferring additional sample holders along said transfer path, said second transfer means including connecting means for connecting said secondary transfer members with said primary transfer member for movement therewith.

38. The device of claim 37, wherein said primary and secondary transfer members transfer said sample holders a predetermined distance along said transfer path during each cycle thereof, said predetermined distance being equivalent to the length of one compartment of the sample holder so that said primary and secondary transfer members engage each of the openings in said sample holders for advancing said sample holders along said transfer path one compartment at a time.

* * * * *

UNITED STATES PATENT AND TRADEMARK OFFICE
CERTIFICATE OF CORRECTION

PATENT NO. : 4,928,453

DATED : May 29, 1990

INVENTOR(S) : Ferkany et al.

It is certified that error appears in the above-identified patent and that said Letters Patent is hereby corrected as shown below:

Claim 13, column 18, line 12, after "said" insert --second--.

Claim 18, column 18, line 57, delete "sup port" and insert --support--.

Signed and Sealed this

Nineteenth Day of May, 1992

Attest:

DOUGLAS B. COMER

Attesting Officer

Acting Commissioner of Patents and Trademarks